(12) United States Patent
Foley et al.

(10) Patent No.: US 6,695,678 B1
(45) Date of Patent: Feb. 24, 2004

(54) MEDICATED BREAST PAD

(75) Inventors: Richard M. Foley, Medfield, MA (US); Kyle A. Nanna, Westwood, MA (US); Sherry Thomas, Hull, MA (US)

(73) Assignee: The First Years Inc., MA (US)

( * ) Notice: Subject to any disclaimer, the term of this patent is extended or adjusted under 35 U.S.C. 154(b) by 0 days.

(21) Appl. No.: 10/395,970

(22) Filed: Mar. 25, 2003

(51) Int. Cl.[7] .................................................. A41C 3/00
(52) U.S. Cl. ............................................. 450/57; 2/267
(58) Field of Search ...................... 450/36–38, 55–57; 2/267, 268; 128/890; 602/41–43, 56; 424/400–402, 420, 443–448, 78.02–78.03; 604/385.07, 358, 363, 364, 368–375, 385.01, 385.03, 385.14, 385.23, 387, 388–390

(56) References Cited

U.S. PATENT DOCUMENTS

| | | | | |
|---|---|---|---|---|
| 2,627,606 A | * | 2/1953 | DeGrandis | 450/57 |
| 2,767,402 A | * | 10/1956 | Pauk | 450/37 |
| 2,891,544 A | * | 6/1959 | London | 450/37 |
| 3,356,090 A | * | 12/1967 | Plantinga et al. | 450/57 |
| 4,047,534 A | * | 9/1977 | Thomaschefsky et al. | 450/57 |
| 4,734,078 A | | 3/1988 | Moreau | |
| 4,748,976 A | * | 6/1988 | Cali | 424/400 |
| 5,017,174 A | * | 5/1991 | Gowrylow | 450/34 |
| 5,281,186 A | | 1/1994 | Buckley et al. | |
| 5,326,305 A | * | 7/1994 | Fochler | 450/57 |
| 5,690,536 A | * | 11/1997 | Madden et al. | 450/37 |
| 5,843,062 A | * | 12/1998 | Reidmiller | 604/378 |
| 5,891,126 A | | 4/1999 | Osborn, III et al. | |
| 5,919,476 A | * | 7/1999 | Fischer et al. | 424/443 |
| 5,964,741 A | | 10/1999 | Moder et al. | |
| 5,968,025 A | | 10/1999 | Roe et al. | |
| 6,039,629 A | * | 3/2000 | Mitchell | 450/57 |
| 6,063,110 A | | 5/2000 | Stedman | |
| 6,074,272 A | * | 6/2000 | Hebert | 450/37 |
| 6,316,524 B1 | | 11/2001 | Corzani et al. | |

FOREIGN PATENT DOCUMENTS

| | | |
|---|---|---|
| WO | WO 95/05095 | 2/1995 |
| WO | WO 01/03748 | 1/2001 |

* cited by examiner

Primary Examiner—Gloria M. Hale
(74) Attorney, Agent, or Firm—Fish & Richardson P.C.

(57) ABSTRACT

A breast pad has a wax-like medicament, such as lanolin, disposed on an exposed surface of an inner liner of the pad in only a limited region, leaving other regions of the inner liner has a permeable region free of the medicament.

20 Claims, 4 Drawing Sheets

MEDICATED BREAST PAD

BACKGROUND

Breast pads sometimes contain a multilayered design, including a non-permeable layer for preventing transfer of breast milk from the liner to clothing, an absorbent layer for holding the milk within the liner, and a wicking layer to draw the liquid away from the breast and into the absorbing layer. A non-permeable layer may also be disposed about the outer periphery of the liner so that a reservoir is formed between the outer surface non-permeable layer and the layer on the periphery for retaining excess milk. An adhesive may be applied to the outer portion of the liner to hold the liner in place in a bra cup. An adhesive may also be used to hold the liner to the breast.

Nursing mothers frequently experience pain and chafing on and around the nipple. Lanolin, also known as wool fat and wool wax, is known to reduce such discomfort. Lanolin is a natural wool grease and originates as a unique substance secreted by sheep from special sebaceous glands in their skin so as to form a natural protective coating on the wool fibers. This unique substance, although derived from an animal, is completely different to the body fat of animals. It has the physical consistency of a soft grease and can also be identified as a wax. The removal of crude wax from the wool by various washing processes and recovery by centrifugal separators gives a product called neutral wool grease, which after intensive refining and a series of other processes, yields a finished purified lanolin. This purified lanolin can reduce a nursing mother's discomfort without affecting a nursing child.

It has been suggested that lanolin, or other medicament, be applied to a breast pad before use. See, for example, U.S. Pat. No. 6,074,272 issued to Hebert.

SUMMARY

Lanolin and some other wax-like medicaments, while very soothing, can impede proper breast pad function, as the medicament can reduce permeability of the inner layer. The invention generally features lanolin or other medicament distributed on a breast pad in improved arrangements that can sooth while enabling good absorption.

According to one aspect, there is a multi-layered breast pad with a non-permeable layer for preventing transfer of breast milk from the liner to clothing, an absorbing layer for holding the milk within the liner and a wicking layer to draw the liquid away from the breast and into the absorbing layer. The exposed surface of the inner layer of the breast pad features a region of lanolin and a lanolin-free region. The lanolin region may enable soothing, while the lanolin-free region enables good absorption.

Preferably, the breast pad includes about 0.03 and 0.15 grams of lanolin, with the lanolin-free region comprising between about 30 and 50 percent of a total exposed surface area of the inner liner. The lanolin may be impregnated into the inner liner, for example. Preferably, the lanolin is in substantially pure form. The lanolin may also be in the form of a coating on the exposed surface of the inner liner or in the form of a dispersion on the exposed surface of the inner liner.

In some embodiments, the limited region of lanolin includes a central portion of the breast pad. The lanolin may be distributed uniformly within the central portion, surrounded by the lanolin-free region. In some cases, the central portion includes both lanolin and lanolin-free areas. Preferably, the lanolin-free region includes a band surrounding the central portion and having a width of at least about 15 millimeters.

In some embodiments, the absorbent layer and wicking layer are of the same material. Various examples include lanolin arranged in selected patterns, including: a concentric ring pattern, discrete channels, or a spiral pattern.

The breast pad may also be provided with an adhesive means (e.g., a pressure sensitive adhesive patch) on a portion of the impermeable outer layer for affixing the pad to clothing.

In another aspect, there is a core containing absorbent material and a liquid impermeable cover disposed on an outer side of the core. An inner surface of the core may contain a wax-like medicament in a limited region, so that the inner surface allows for permeability through a remaining medicament-free region. The wax-like medicament may comprise lanolin.

Another aspect includes an inner surface for contacting a mammary gland with a first region having a wax-like medicament and a second region that is free of wax-like medicaments and permeable to fluids.

In an additional aspect, there is a method of absorbing mammary fluids while soothing skin that includes placing the breast pad on a human mammary gland such that the first region contacts at least a portion of an areola of the mammary gland.

The details of one or more embodiments of the invention are set forth in the accompanying drawings and the description below. Other features, objects, and advantages of the invention will be apparent from the description and drawings, and from the claims.

DESCRIPTION OF DRAWINGS

Like reference symbols in the various drawings indicate like elements.

DETAILED DESCRIPTION

Figure 1:
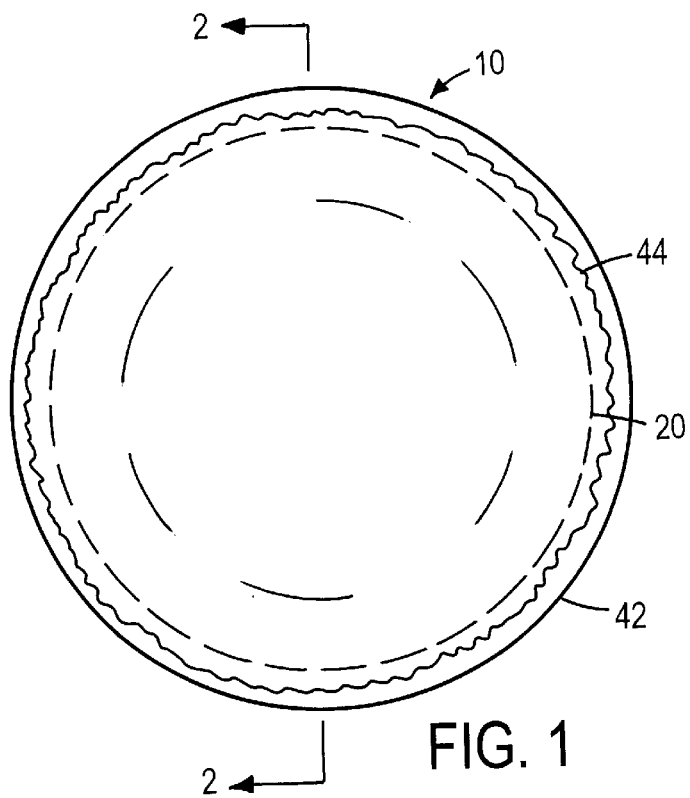
FIG. 1 is a frontal view of a breast pad.
Figure 2:
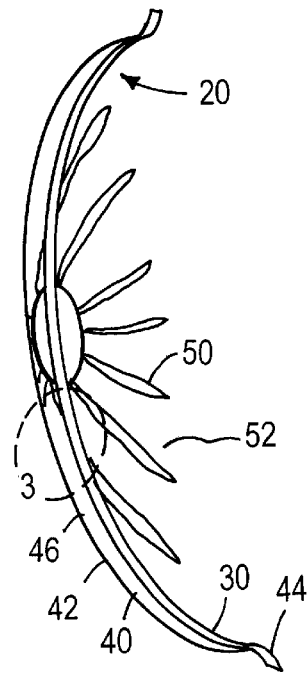
FIG. 2 is a side view of the breast pad of FIG. 1.

Referring to the drawings in detail and to FIGS. 1 and 2 in particular, a breast pad 10 is a contoured circular shaped device to be inserted into the cup of a bra or into the clothing of the user. The breast pad 10 generally includes an inner liner 20, a wicking layer 30, an absorbent layer 40, and an outer cover 42. The wicking layer 30 and the absorbent layer 40 are sandwiched between the inner liner 20 and the outer cover 42. Lanolin 50 is disposed on an exposed surface of the inner liner in only a limited region thereof, such that the inner liner has a lanolin-free region for permeability. It should be noted that the breast pad 10 is preferably for lining the interior of a bra, but may also be used without a bra if held in place by a user's clothing or by some other means such as an adhesive.

The inner liner 20 is generally a soft permeable material for contact with the user's breast. The inner liner 20 allows fluid to flow through it to the wicking layer 30 while remaining dry and comfortable against the user's breast.

This material may be similar to a stay-dry lining found in disposable diapers. The inner liner 20 and the outer cover 42 are joined to each other at their periphery, such as by stitching, heat sealing, or ultrasonic bonding 44. Sealed edges provide perimeter leak protection.

The wicking layer 30 acts to quickly draw moisture away from the breast. The wicking layer 30 is generally a soft fiber fill material.

The absorbent layer 40, residing between the outer cover 42 and the wicking layer 30, is for absorbing fluids leaking from the user's breast. The absorbent layer 40 is generally made of a sheeted air laid cellulose material. The absorbent layer 40 may also be made of naturally absorbent materials such as cotton, cellulose, and the like. The absorbent material 40 may also be made from other natural or synthetic materials such as silica gel, thermoplastic, copolymers, foam or similar materials. Many materials that contain or have been impregnated with a jelling agent such as polyacrylate granted starch or maleic anhydride-based copolymers may be used to absorb the fluid. Some of the jelling agent impregnated materials will absorb the greatest amount of fluid with the least amount of expansion. Antibacterial agents or deodorant such as baking soda may be added to the absorbent layer 40 to reduce odor from the fluid that accumulates.

Figure 3:
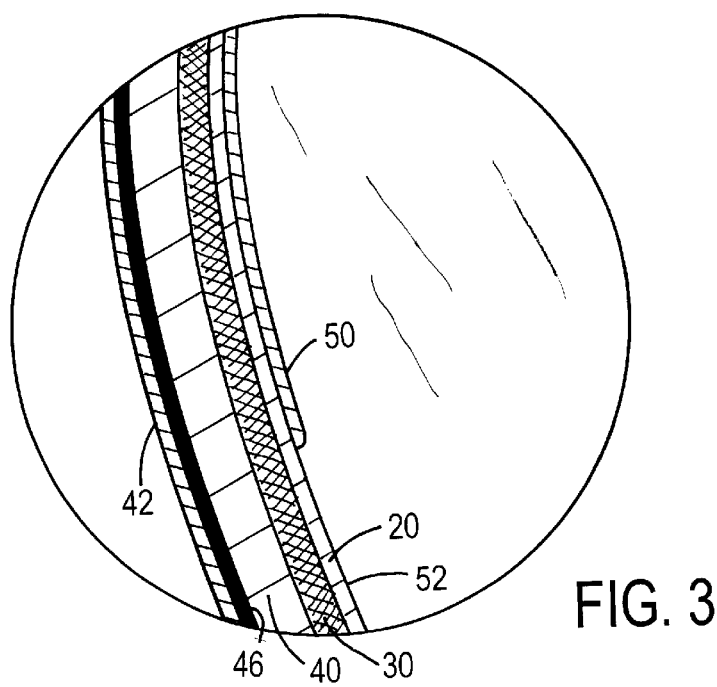
FIG. 3 is an is an enlarged view of area 3 of FIG. 2.

Referring to FIGS. 2 and 3, the outer cover 42 and the absorbent layer 40 are joined to each other with an adhesive medium 46. The adhesive medium 46 prevents leaks by holding the outer cover 42 and the absorbent layer 40 central to one another. The adhesive medium 46 is applied in a manner that is consistent with the size and shape of the absorbent layer 40, so as to allow an even, approximately 0.5 inch, seal 44 of the inner liner 20 and the outer cover 42 to be created about the entire periphery of the breast pad 10.

The outer cover 42 is generally a non-permeable material such as a breathable barrier flexible film, a spun-bond polypropylene laminated onto a film layer, or a dense fabric. The outer cover 42 is the farthest away a user's breast and remains in contact with an inside of a bra cup when the breast pad 10 is in use. The outer cover 42 may also be made of a semi-permeable material for preventing fluid from passing while allowing air to flow through the material. In this way any liquid leaking from the user's breast would be separated from the user's clothing, but air could pass through the breast pad 10, thereby making the user more comfortable. The outer cover 42 can be of any material known in the art.

The inner liner 20 of the breast pad 10 has lanolin 50 disposed on an exposed surface of the inner liner 20 in only a limited region thereof, such that the inner liner 20 has a lanolin-free region 52 for permeability. In this example, lanolin 50 is disposed in a star pattern with arms radiating from the center of the breast pad 10.

Figure 4A:
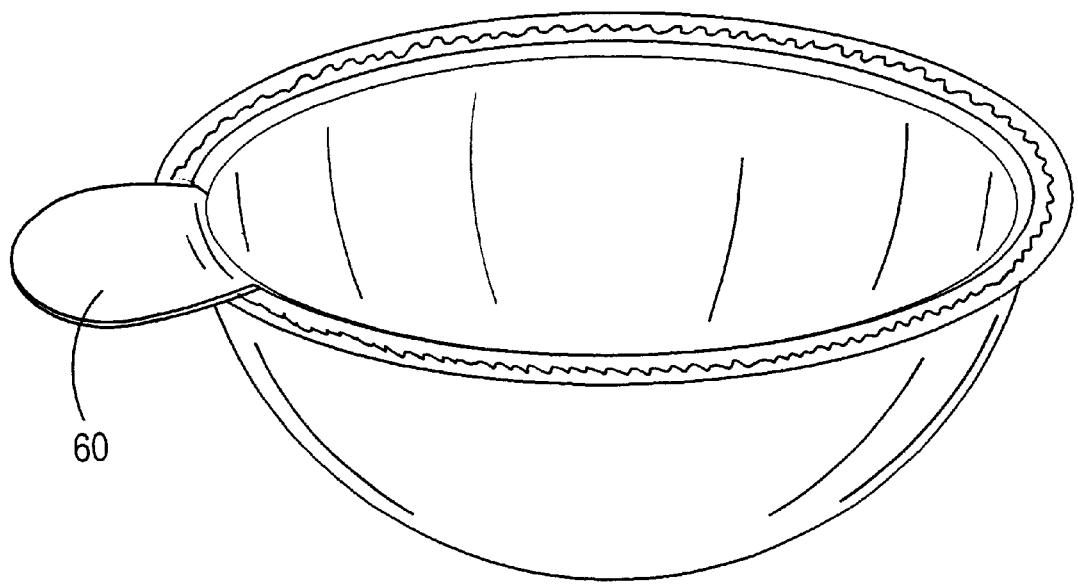
FIGS. 4A and 4B show a perspective view of the breast pad of FIG. 1.
Figure 4B:
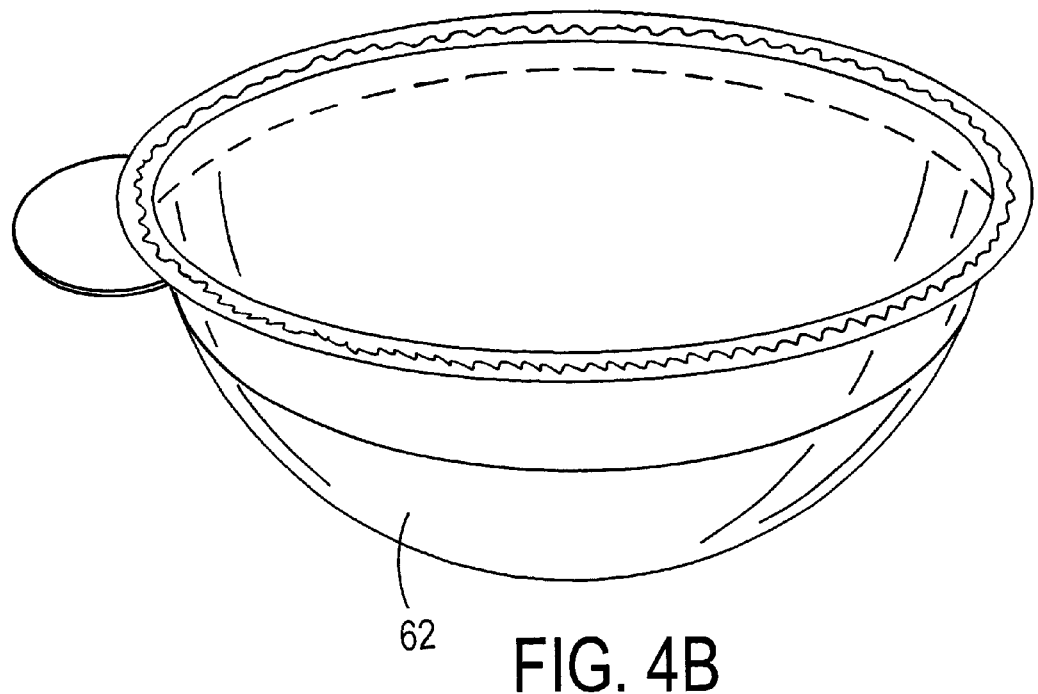

Referring to FIG. 4A, the breast pad 10 may also include an inside cover 60 for protecting the inner liner 20, and the lanolin 50 thereon, when it is packaged or otherwise out of contact with the user's breast. Referring to FIG. 4B, an outside cover 62 may also preserve a means for attaching the liner to an outer garment or inside of a bra. An adhesive material may be disposed on the outer cover 42 of the breast pad 10. The adhesive material would insure that the breast pad does not slide around within a bra or other undergarment.

The lanolin 50 residing on the inner liner 20 may be in substantially pure form or be mixed with other medicaments or substances. The lanolin 50 may be in the form of a coating or in the form of a dispersion on the exposed surface of the inner liner 20. The lanolin 50 may also be impregnated or embedded within the inner liner 20 itself. The amount of lanolin 50 residing on or within the inner liner 20 should be selected to prevent run-off of the lanolin 50 beyond the confines of the breast pad 10, while maximizing the amount of lanolin in contact with the breast and permitting an acceptable level of milk absorption into the pad. To maximize contact with the breast, there is in some embodiments lanolin 50 covering about one-half of the area of the inner liner 20.

To avoid excessive run-off of the lanolin 50 due to high temperatures during shipment and storage, and to promote absorption of mammary fluids into the pad, we prefer to have at least about a 19 millimeter wide band of substantially medicament-free inner liner surface surrounding any central portion of inner liner substantially covered with lanolin or other wax-like medicament. For substantially pure lanolin, we prefer an application of only between about 0.09 and 0.11 grams of lanolin per pad, distributed primarily in a central region 74 surrounded by a substantially lanolin-free region 79 (see FIG. 8). The lanolin 50 may be uniformly distributed across such a central region 74, for example. In one instance, a breast pad has an inner liner of about 100 millimeters in diameter (the pad having a total diameter of about 115 millimeters), with lanolin 50 evenly distributed only in a central region 74 having a diameter of about 63 millimeters, leaving a 19 millimeter wide lanolin-free outer band 79 of the inner liner with enhanced absorption characteristics.

In one example, the inner liner 20 is 0.3–0.5 ounces per square yard (osy) of a meltblown and spun-bonded polypropylene fabric manufactured by BBA Nonwovens Reemay, Inc. The wicking layer 30 is 2.5–3.0 osy of a kneedle punched polyethylene fabric sheet approximately 0.1875 inch thick manufactured by FiberVisions of Athens, Ga. and marketed as its Polyolefin Fiber. The absorbent layer 40 is a cellulose material, air laid, fabric sheet with homogenized super absorbent gel beads having an average absorption in the range of 55–75 mL of water manufactured by Buckeye Technologies Inc. of Memphis, Tenn. and marketed as its Vizorb Plus 3905. The outer cover 42 is 1.0 osy of a breathable barrier film, where 0.5 osy of a polypropylene spun-bond fabric is laminated onto 0.5 osy of a polypropylene film layer manufactured by Clopay Plastic Products Co. of Mason, Ohio under part number P18-5076 (01043001). The lanolin 50 is 100% pure medical grade USP modified lanolin manufactured by Croda Inc. of Mill Hall, Pa. and marketed as Westbrook Medilan under part number MDLN. The lanolin 50 has a minimum water absorption of 200% and a maximum 1 part per million of total pesticide residues. Its melting point drop ranges from 38–43 degrees Celsius.

Figure 5:
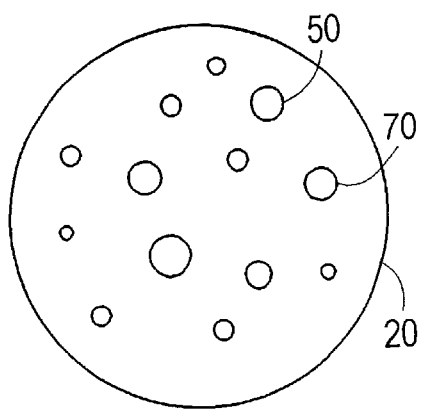
FIGS. 5–13 show various patterns of medicament on the inner surface of the breast pad.
Figure 6:
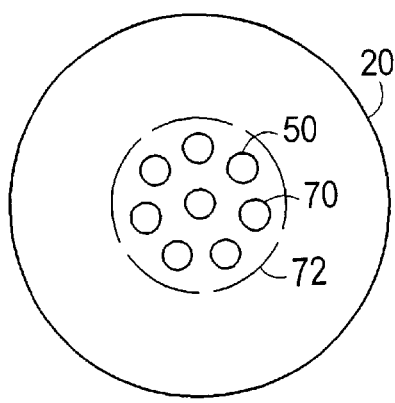

Referring to FIG. 5, in another example lanolin 50 is disposed on the inner liner 20 of the breast pad in a random form of small globules 70 around an entire area of the inner liner 20 of the breast pad 10. FIG. 6 provides another example where the lanolin 50 is disposed on the inner liner 20 of the breast pad 10, but here the random pattern of small globules 70 is limited to a central portion 72 of the breast pad. The central portion 72 of the breast pad is preferably large enough to cover an areola of a typical user's breast. This allows for soothing of cracked skin irritated due to suckling.

Figure 7:
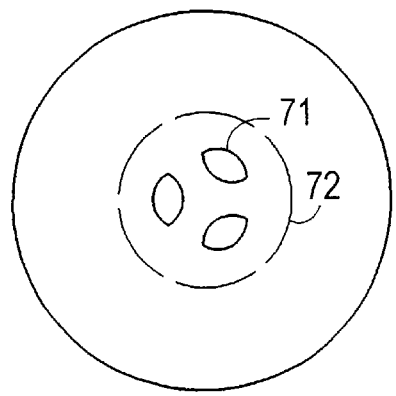
Figure 8:
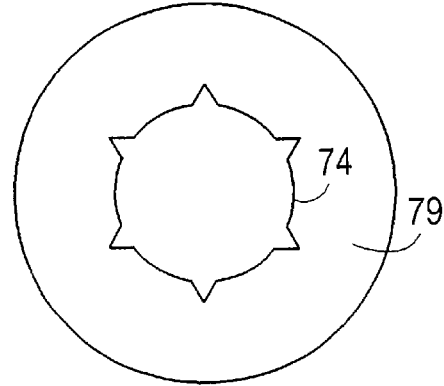

Referring to FIG. 7, lanolin is disposed on the inner liner 20 of the breast pad in a pre-selected pattern of discrete regions 71 within the central portion 72 of the breast pad. The lanolin of FIG. 8 is disposed in a large dispersion 74 covering substantially the central portion of another breast pad, leaving an outer band of lanolin-free area 79.

Figure 9:
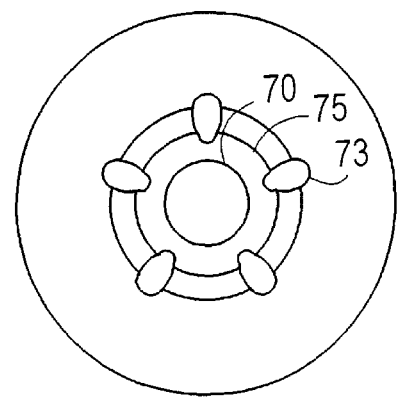
Figure 10:
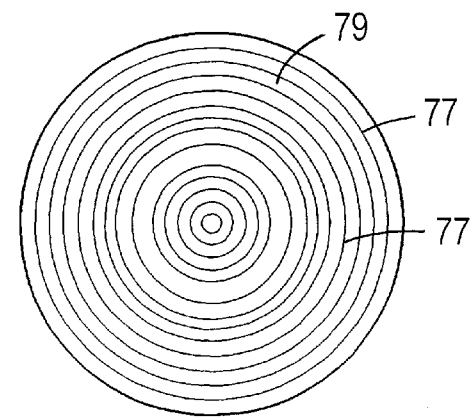
Figure 11:
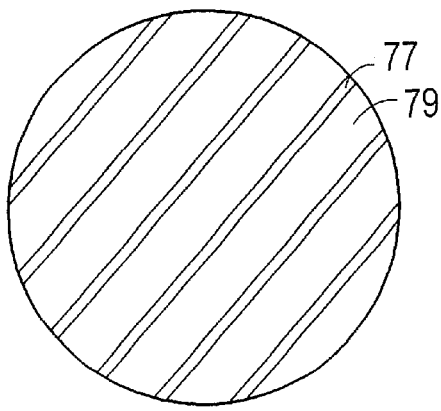
Figure 12:
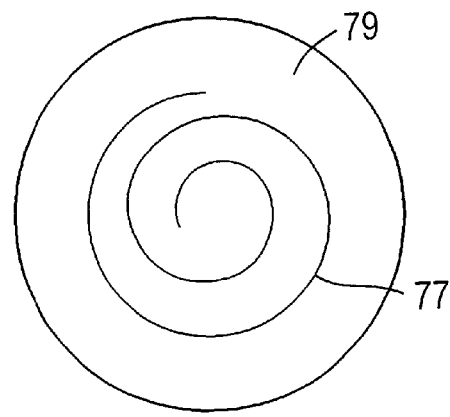
Figure 13:
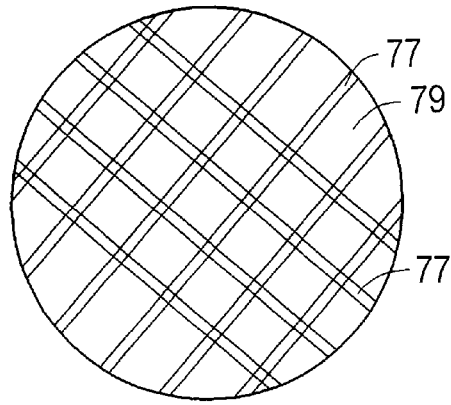

Referring to FIG. 9, lanolin is distributed on the inner liner 20 of another breast pad in narrow regions 73 extending radially the central portion of the breast pad, each region 73 crossing a narrow ring 75 of lanolin surrounding a central dot 70 of lanolin. The remainder of the inner surface of the pad is free of lanolin. In FIG. 10, lanolin is disposed on the inner liner of another breast pad in a concentric ring pattern. FIG. 11 shows an inner breast pad surface with lanolin distributed in spaced-apart lines 77 extending across the entire breast pad surface. In FIG. 12, lanolin is disposed on the inner breast pad surface in a spiral pattern. In FIG. 13, lanolin is disposed on the inner liner of a breast pad in intersecting grid lines 77, bounding discrete lanolin-free, absorbent regions 79.

Referring to FIGS. 5–3, where the lanolin 50 is impregnated or embedded within the inner liner 20, small particles or droplets of lanolin are distributed throughout the inner liner in either an even or random distribution in roughly the patterns described above but limited by the confines of the weave of the material of the inner liner. Where the woven material creates square spaces between fibers, the impregnation or embedding of the lanolin will appear in a checkerboard pattern. Fibers in the inner liner may not bond to the lanolin, but they may entangle with each other resulting in suitable securement between them. The lanolin remains entrapped within the inner liner until the composition experiences shearing forces created by application of the composition on the breast. At this point, the entrapped lanolin has few physical barriers to prevent its coalescence to the skin.

A number of embodiments of the invention have been described. Nevertheless, it will be understood that various modifications may be made without departing from the spirit and scope of the invention. Accordingly, other embodiments are within the scope of the following claims.

What is claimed is:

1. A breast pad comprising:
   an outer cover of fluid impermeable material;
   an inner liner joined to the outer cover in a peripheral region of the breast pad;
   a wicking layer sandwiched between the inner liner and the outer cover for drawing in fluid entering the pad through the inner liner;
   an absorbent layer sandwiched between the wicking layer and the outer cover for absorbing fluid entering the pad; and
   lanolin disposed on an exposed surface of the inner liner in only a limited region thereof, such that the inner liner has a lanolin-free region for permeability.

2. The breast pad of claim 1 comprising between about 0.03 and 0.15 grams of lanolin.

3. The breast pad of claim 1 comprising between about 0.09 and 0.11 grams of lanolin.

4. The breast pad of claim 1 wherein the lanolin-free region comprises between about 30 and 50 percent of a total exposed surface area of the inner liner.

5. The breast pad of claim 1 wherein the lanolin-free region comprises between about 35 and 45 percent of a total exposed surface area of the inner liner.

6. The breast pad of claim 1 wherein at least about 50 percent of a total exposed surface area of the inner liner is lanolin-free.

7. The breast pad of claim 1 wherein the limited region of lanolin includes a central portion of the breast pad.

8. The breast pad of claim 7 wherein the lanolin is distributed uniformly within the central portion.

9. The breast pad of claim 8 wherein the central portion is surrounded by the lanolin-free region.

10. The breast pad of claim 9 wherein the lanolin-free region has a width of at least about 15 millimeters.

11. The breast pad of claim 7 wherein the central portion includes both lanolin and lanolin-free areas.

12. The breast pad of claim 1 wherein the absorbent layer and the wicking layer are of the same material.

13. The breast pad of claim 1 wherein the lanolin is in substantially pure form.

14. The breast pad of claim 1 wherein the lanolin is in the form of a coating on the exposed surface of the inner liner.

15. The breast pad of claim 1 wherein lanolin is in the form of a dispersion oil the exposed surface of the inner liner.

16. The breast pad of claim 1 wherein the lanolin is arranged in a concentric ring pattern.

17. The breast pad of claim 1 wherein the lanolin is arranged in discrete channels.

18. The breast pad of claim 1 wherein the lanolin is arranged in a spiral pattern.

19. The breast pad of claim 1 having an adhesive means on a portion of said fluid impermeable outer layer for affixing the pad to clothing.

20. The breast pad of claim 1 wherein the lanolin is impregnated within the inner liner.

* * * * *

UNITED STATES PATENT AND TRADEMARK OFFICE
CERTIFICATE OF CORRECTION

| | |
|---|---|
| PATENT NO. | : 6,695,678 B1 |
| DATED | : February 24, 2004 |
| INVENTOR(S) | : Richard M. Foley, Kyle A. Nanna and Sherry Thomas |

It is certified that error appears in the above-identified patent and that said Letters Patent is hereby corrected as shown below:

Title page,
Item [56], References Cited, U.S. PATENT DOCUMENT,
"5,017,174 A * 5/1991  Gowrylow.......450/34" should read -- 5,017,174 A * 5/1991 Gowrylow.......450/37 --;

Column 5,
Line 36, please replace "oil" with -- on --.

Signed and Sealed this

Thirteenth Day of July, 2004

JON W. DUDAS
*Acting Director of the United States Patent and Trademark Office*